United States Patent [19]

Kisfaludy et al.

[11] 4,428,938
[45] Jan. 31, 1984

[54] PEPTIDES AFFECTING THE IMMUNE REGULATION AND A PROCESS FOR THEIR PREPARATION

[75] Inventors: Lajos Kisfaludy; Olga Nyéki née Kuprina; István Schőn; Laszlo Dénes; Julia Ember; György Hajós; László Szporny; Béla Szende, all of Budapest, Hungary

[73] Assignee: Richter Gedeon Vegyeszeti Gyar Rt., Budapest, Hungary

[21] Appl. No.: 387,655

[22] Filed: Jun. 11, 1982

[30] Foreign Application Priority Data

Jun. 12, 1981 [HU] Hungary ............................ 1755/81

[51] Int. Cl.$^3$ ..................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS 4,190,646  2/1980  Goldstein et al. ........... 260/112.5 R
4,261,886  4/1981  Goldstein et al. ........... 260/112.5 R

OTHER PUBLICATIONS

Chemical & Pharmaceutical Bulletin 28, No. 8, (1980) 2507–2511.

*Primary Examiner*—Delbert R. Phillips
*Attorney, Agent, or Firm*—Karl F. Ross; Herbert Dubno

[57] ABSTRACT

Peptides affecting the immune regulation selected from the following group:
Arg-Lys-Asp
Arg-Lys-Asp-Val
Arg-Lys-Asn-Val
Arg-Lys-Asu-Val
Arg-Lys-Ala-Val
Arg-Lys-Asp-Ala
Arg-Lys-Asp-Ile
Arg-Lys-Glu-Val
Arg-Ala-Asp-Val
Arg-Asp-Lys-Val
Ala-Lys-Asp-Val
Lys-Arg-Asp-Val
Glp-Arg-Lys-Asp
Glp-Arg-Lys-Asp-Val
Glp-Arg-Lys-Asp-Val-Tyr and salts, amides lower alkyl esters and protected derivatives thereof.

3 Claims, No Drawings

PEPTIDES AFFECTING THE IMMUNE REGULATION AND A PROCESS FOR THEIR PREPARATION

FIELD OF THE INVENTION

The invention relates to new peptides having an influence on immune regulation and a process for the preparation thereof.

BACKGROUND OF THE INVENTION

Tests carried out in the past few years have revealed that thymus hormones directly participate in processes regulating the T-lymphocyte-dependent immunological equilibrium. They appear to convert the young T-cells into ripe, differentiated cells which have a central role in cell-mediated immunity and in the regulation of various immune responses. The thymus hormones exert their activity not only inside but also outside the thymus and play a role in the formation of cytotoxic, supressant and helper cells. The promising results of the first clinical tests carried out by thymus extracts on patients suffering from immune deficiency or cancer gave a further impulse to the research activity in this field. It has further been revealed that in the case of DiGeorge syndrome, IgA deficiency and general skin tuberculosis the thymus level of the serum decreases while in the case of rheumatoid arthritis the increase of thymus level has been observed. It can, therefore, reasonably be concluded that the regulation of the hormone level will have a favorable influence on these diseases [E. Arrigoni-Martelli: Drugs of Today 16, 203 (1980)].

One of the thymus hormones which has been isolated as a uniform product, structurally identified and even synthesized is thymopoietine [Goldstein et al: Nature 247, 11 (1974); Goldstein et al: Ann. N. Y. Sci. 249, 177 (1975); U.S. Pat. Nos. 4,002,740 and 4,077,949] consisting of 49 amino acids. Tests carried out with the natural and then the synthetic product [Fujino et al: Chem. Pharm. Bull. 25, 1486 (1977); Bliznakov et al: Biochem. Biophys. Res. Commun. 80, 631 (1978)] unambiguously show that thymopoietine induces the differentiation of the T-cells in vitro and in vivo as well.

Due to the restricted natural resources of thymopoietine which are not sufficient to meet the great demands and the high price of the synthetic product an extensive research activity has been initiated to determine the active center of thymopoietine. At first a tridecapeptide, thymopoietine(24–41) [Schlesinger et al: Cell 5, 631 (1978)] and then a pentapeptide, thymopoietine(3-2-36) (designated as TP5) were reported to possess all biological properties of the complete hormone [Goldstein et al: Science 204, 1309 (1979); U.S. Pat. No. 4,190,646]. Recently certain fragments and analogs of TP5 have also been described which were, however, ineffective in the test system [Abiko et al: Chem. Pharm. Bull. 28, 2507 (1980)].

We have found that if the TP5 chain is shortened starting from the C-terminal moiety and not from the N-terminal moiety as suggested by the Japanese authors [Abiko et al: Chem. Pharm. Bull. 28, 2507 (1980)], the Arg-Lys-Asp-Val tetrapeptide and even the Arg-Lys-Asp tripeptide is active, i.e. increases the number of the lymphocytes forming the E-rosette.

DESCRIPTION OF THE INVENTION

The present invention concerns the synthesis of the above tetra- and tripeptides and certain analogs thereof. It has surprisingly been found that certain analogs show an adverse biological activity. This is the first experimental proof of the fact that the immune response inducing and inhibiting activities are connected with closely related structural elements. All compounds prepared according to the instant invention are new.

The new compounds according to the invention are synthesized in a solution, stepwise, following conventional techniques of the peptide chemistry. The combination of protecting groups used during the synthesis allows the selective elimination of the protecting groups, most preferably in a single step. In most of the cases the peptide bond was formed by our pentafluorophenyl ester procedure [Kisfaludy et al: Hungarian Patent Specification No. 168,431; and Kisfaludy et al: Tetrahedron Letters 1785 (1974)].

The invention relates to new peptides having an influence on the immune regulation and a process for the preparation thereof. More particularly, the invention concerns the following new peptides:

Arg-Lys-Asp
Arg-Lys-Asp-Val
Arg-Lys-Asn-Val
Arg-Lys-Asu-Val
Arg-Lys-Ala-Val
Arg-Lys-Asp-Ala
Arg-Lys-Asp-Ile
Arg-Lys-Glu-Val
Arg-Ala-Asp-Val
Arg-Asp-Lys-Val
Ala-Lys-Asp-Val
Lys-Arg-Asp-Val
Glp-Arg-Lys-Asp
Glp-Arg-Lys-Asp-Val
Glp-Arg-Lys-Asp-Val-Tyr and their salts, amides, lower alkyl esters or protected derivatives. The new peptides according to the invention are synthesized by the conventional techniques of peptide chemistry and if desired, the protecting groups can be eliminated from the protected derivatives. The term "lower alkyl" is used herein to refer to alkyl groups having 1 to 4 carbon atoms.

According to a preferred embodiment of the process the tetrapeptide Arg-Lys-Asp-Val is synthesized as follows: L-valine p-nitro-benzylester is acylated by N-tert.-butyloxycarbonyl-L-asparaginic acid β-benzylester-α-pentafluorophenylester, from the protected dipeptide obtained the tert.-butyloxycarbonyl group is selectively eliminated, whereupon the free dipeptide is acylated by N-α-tert.-butyloxycarbonyl-N-ε-benzyloxycarbonyl-L-lysine-pentafluorophenyl ester. Treatment of the protected tripeptide with trifluoroacetic acid provides a tripeptide free at the N-terminal moiety, which is then acylated with N-benzyloxycarbonyl-O-nitro-L-arginine-pentafluorophenyl ester. All protecting groups of the protected tetrapeptide obtained may be eliminated in a single step, by catalytic hydrogenation. The free peptides obtained generally do not require further purification. In certain cases the free peptides are purified by chromatography on a silica gel column. The end product is then isolated by evaporation or lyophylization. The peptides obtained can be converted into the desired salts or complex derivatives.

The biological investigation of the peptides according to the invention was performed by the following test methods:

I. In vitro method

The active E-rosette test was carried out according to a modified method of Wybran et al [Wybran et al: New Engl. J. Med. 292, 475 (1975)] by the lymphocites of healthy and autoimmune patients (rheumatoid arthritis and systemic lupus erythematosus). To 50 μl of a lymphocyte cell suspension $10^{-3}$–$10^{-11}$ moles/lit. solutions of the test material were added and the mixture was incubated in an atmosphere containing 5.0% of carbon dioxide, at 37° C. for 60 minutes. Thereafter 50 μlit. of a 1% sheep erythrocite suspension were added and the mixture was centrifuged at 1000 r.p.m. for 10 minutes followed by shaking with a modified Gallenkampf-shaker (shaking time: 30 sec, stroke: 8 cm, shaking frequency: 65/min.). The rosettes were fixed with a 0.1% glutaric aldehyde (50 μlit. for each tube, 3 min.). Lymphocytes bonding more than three sheep erythrocite were counted under a microscope and 4×100 cells were evaluated. The separated lymphocytes contain macrophages and polymorphonuclear cells (up to 10%) as an impurity. The number of the cells forming the rosettes was corrected by this value each case. The results are set forth in Tables 1 and 2.

II. In vitro method (1) The effect on antibody production was tested according to Ceglowski's method [Ceglowski: Ann. N.Y. Acad. Sci. 249, 343 (1975)]. New-born H. Wistar rats were treated with single 25 μlit. doses of $4\times10^{-3}$–$4\times10^{-7}$ moles/lit. of the test material (9 animals for each dose) at the latest at the 12th hour after birth. The 14-day animals were then immunized with a sheep erythrocyte suspension administering 0.5 ml. of a 5% sheep erythrocyte suspension each animal intraperitoneally. On the 7th day after immunization the animals were decapitated. The blood of three animals was mixed and from the serum obtained (after centrifuging at 3000 r.p.m. for 10 minutes) the titers for antibodies were determined by the method of Takátsy [Takátsy: Acta Microbiol. Acad. Sci. Hung. 3, 191 (1955)]. The results are expressed in agglutination titers. The titer corresponds to the lowest dilution of the serum in which agglutination can be observed. The results are given in the Table 3.

(2) The number of the cells producing a specific antibody was determined by the method of Canningham Handbook of Experimental Immunology (editor: D. M. Weir), 2nd Volume, p. 285, Blackwell, Oxford-London (1978). According to this method from the spleen cells of immunized animals, sheep erythrocyte suspension and complement a homogenous suspension was prepared and it was placed into a chamber suitable for forming a single cell layer. Around the spleen cells lytic areolas are formed, the number of which is identical with the number of the cells producing a specific antibody (plaque forming cells, PFC).

The test animals, not later than 12 hour after birth, were given a single i.p. dose of the test material. According to the method (1) three different doses of each substance were tested. On the 7th day after immunization the plaque formation of the spleen cells isolated from the animals was examined. The ratio of the plaque formation produced by the treated and untreated (control) animals is given in Table 4.

TABLE 1

The E-rosette forming activity of the lymphocytes of patients suffering from rheumatoid arthritis*

| | | Doses(-xlg moles/liter) | | | | | |
|---|---|---|---|---|---|---|---|
| | | 0 | 11 | 9 | 7 | 5 | 3 |
| 1. | Arg—Lys—Asp—Val—Tyr(TP5) | 23.6 | 26.7 | 26.8 | 29.9 | 26.7 | — |
| 2. | Arg—Lys—Asp—Val | 29.4 | 32.6 | 36.8 | 34.4 | 31.5 | 36.2 |
| 3. | Arg—Lys—Asp++ | 26.4 | 28.4 | 30.7 | 28.8 | 28.6 | 27.2 |
| 4. | Arg—Lys—Asp—Val—NH$_2$ | 26.4 | 28.2 | 34.8 | 26.9 | 29.8 | 31.5 |
| 5. | Lys—Arg—Asp—Val | 20.8 | 26.6 | 25.7 | 21.2 | 25.8 | 23.6 |
| 6. | Arg—Lys—Asp—Val—OMe | 26.4 | 26.5 | 27.9 | 32.4 | 30.8 | 31.2 |
| 7. | Glp—Arg—Lys—Asp—Val | 23.7 | 20.4 | 19.4 | 21.4 | 23.2 | 22.8 |
| 8. | Glp—Arg—Lys—Asp++ | 23.7 | 18.4 | 19.7 | 19.5 | 18.7 | 20.6 |
| 9. | Arg—Lys—Asn—Val | 27.7 | 24.3 | 23.7 | 24.6 | 21.9 | 22.3 |
| 10. | Arg—Lys—Asu—Val | 20.8 | 25.0 | 28.6 | 24.3 | 22.5 | 23.6 |
| 11. | Arg—Ala—Asp—Val | 23.7 | 22.5 | 20.7 | 19.8 | 20.2 | 21.8 |
| 12. | Arg—Lys—Ala—Val | 20.8 | 23.1 | 25.5 | 21.7 | 23.4 | 20.3 |
| 13. | Ala—Lys—Asp—Val | 23.7 | 20.3 | 23.9 | 22.5 | 22.8 | 25.3 |
| 14. | Arg—Lys—Asp—Ala | 26.4 | 27.9 | 25.3 | 25.8 | 24.5 | 28.6 |
| 15. | Arg—Lys—Asp—Ile | 27.7 | 24.5 | 28.7 | 23.2 | 25.4 | 25.5 |
| 16. | Arg—Asp—Lys—Val | 27.7 | 27.5 | 27.3 | 26.4 | 26.2 | 25.4 |
| 17. | Glp—Arg—Lys—Asp—Val—Tyr | 20.8 | 24.9 | 26.6 | 22.6 | 22.7 | 24.1 |

*The percentage amount of active lymphocytes /n = 4/;
++P 0.05 F test (compared to TP5 by 1 aspect variancy analysis); P 0.05 by student t test

TABLE 2

The E-rosette forming activity of the lymphocytes of healthy persons*

| | | Doses (-xlg moles/liters) | | | | | |
|---|---|---|---|---|---|---|---|
| | | 0 | 11 | 9 | 7 | 5 | 3 |
| 1. | Arg—Lys—Asp—Val—Tyr(TP5) | 27.8 | 25.2 | 27.1 | 24.4 | 23.7 | 29.4 |
| 2. | Arg—Lys—Asp—Val++ | 33.8 | 33.7 | 43.0 | 38.5 | 39.1 | 41.3 |
| 3. | Arg—Lys—Asp | 30.3 | 35.9 | 39.3 | 41.7 | 34.1 | 29.9 |
| 4. | Arg—Lys—Asp—Val—NH$_2$ | 30.3 | 38.1 | 26.6 | 35.1 | 33.8 | 29.0 |
| 5. | Arg—Lys—Asp—Ala | 35.3 | 40.5 | 36.4 | 40.8 | 39.6 | 41.2 |
| 6. | Ala—Lys—Asp—Val | 35.3 | 36.2 | 39.1 | 47.5 | 34.9 | 43.4 |
| 7. | Arg—Lys—Asp—Val—OMe | 29.7 | 23.8 | 24.8 | 29.4 | 27.2 | 26.8 |
| 8. | Arg—Asp—Lys—Val+++ | 32.1 | 36.4 | 40.4 | 37.7 | 37.5 | 34.2 |
| 9. | Glp—Arg—Lys—Asp | 30.3 | 38.1 | 26.6 | 35.1 | 33.8 | 29.1 |
| 10. | Arg—Lys—Ala—Val | 34.7 | 30.9 | 34.5 | 35.8 | 30.5 | 33.3 |

TABLE 2-continued

The E-rosette forming activity of the lymphocytes of healthy persons*

| | | Doses (-xlg moles/liters) | | | | |
|---|---|---|---|---|---|---|
| | | 0 | 11 | 9 | 7 | 5 | 3 |
| 11. | Arg—Ala—Asp—Val | 34.7 | 36.0 | 38.2 | 32.4 | 33.4 | 32.5 |
| 12. | Lys—Arg—Asp—Val | 28.9 | 32.9 | 29.1 | 30.0 | 25.6 | 31.5 |
| 13. | Arg—Lys—Asu—Val | 29.7 | 31.5 | 32.3 | 29.0 | 29.7 | 29.3 |
| 14. | Arg—Lys—Glu—Val[++] | 31.9 | 33.0 | 35.4 | 36.2 | 32.9 | 33.2 |
| 15. | Arg—Lys—Asn—Val[++] | 32.1 | 36.7 | 35.4 | — | 39.1 | 35.5 |
| 16. | Arg—Lys—Asp—Ile[++] | 33.2 | 30.7 | 35.0 | 34.9 | 32.0 | 35.5 |
| 17. | Glp—Arg—Lys—Asp—Val—Tyr | 24.1 | 29.9 | 25.5 | 29.4 | 22.5 | 29.9 |

*The percentage amount of active lymphocytes /n = 4/;
[++]P 0.05 F test (by one aspect variancy analysis compared to TP5);
[+++]P 0.01 F test (by one aspect variancy analysis compared to TP5); P 0.05 Student t significant effect

TABLE 3

In vitro effect on the antibody production[+] expressed in the agglutination titer

| | Dose (moles/liter) | | | | | | |
|---|---|---|---|---|---|---|---|
| | $4 \cdot 10^{-3}$ | $4 \cdot 10^{-4}$ | $4 \cdot 10^{-5}$ | $4 \cdot 10^{-6}$ | $4 \cdot 10^{-7}$ | $4 \cdot 10^{-8}$ | 0 |
| Arg—Lys—Asp—Val—Tyr(TP5) | 12.0 ± 0 | 8.7 ± 2.3 | 10.7 ± 2.3 | 9.0 ± 1.7 | — | — | 9.3 ± 1.5 |
| Arg—Lys—Asp—Ala[++] | 10.5 ± 1.5 | — | 11.5 ± 0.9 | — | 12.0 ± 0 | — | 9.3 ± 1.5 |
| Arg—Lys—Asp[++] | — | 6.0 ± 0 | — | 7.3 ± 0.6 | — | 6.0 ± 1.2 | 5.2 ± 1.3 |
| Arg—Lys—Asp—Val—NH$_2$ | — | 5.2 ± 2.2 | — | 6.2 ± 2.0 | — | 6.8 ± 0.8 | 5.2 ± 1.3 |
| Glp—Arg—Lys—Asp—Val—Tyr[++] | 3.0 ± 1.0$^x$ | — | 5.2 ± 0.8$^x$ | — | — | — | 5.2 ± 1.3 |
| 5.5 ± 0.6$^y$ | | | | | | | |
| Glp—Arg—Lys—Asp—Val | 9.0 ± 2.6 | — | 8.3 ± 0.6 | — | 7.2 ± 1.3 | — | 9.3 ± 1.5 |
| Arg—Lys—Asp—Val—OMe | 6.0 ± 1.7 | — | 4.5 ± 0.5 | — | 5.5 ± 2.6 | — | 5.2 ± 1.3 |

[+]Antibody-titer = $\bar{X}$ ± S.D.
[++]P 0.05 Student t test
$^x$The concentration of the test material is half of the value indicated in the head of the column
$^y$Concentration $2 \cdot 10^{-1}$ moles/liter

TABLE 4

Effect on plaque forming spleen cells (PFC)

| | Dose (mmoles) | Number of PFC cells (treated) Number of PFC cells (untreated) |
|---|---|---|
| Arg—Lys—Asp | $1.0 \cdot 10^{-4}$ | 0.7 |
| | $1.0 \cdot 10^{-6}$ | 2.1 |
| | $1.0 \cdot 10^{-8}$ | 1.8 |
| Arg—Lys—Asp—Val—NH$_2$ | $1.0 \cdot 10^{-4}$ | 0.3 |
| | $1.0 \cdot 10^{-6}$ | 0.52 |
| | $1.0 \cdot 10^{-8}$ | 2.7 |
| Arg—Lys—Asp—Val | $2.5 \cdot 10^{-3}$ | 0.34 |
| | $2.5 \cdot 10^{-4}$ | 0.8 |
| Arg—Lys—Asp—Ala | $1.0 \cdot 10^{-4}$ | 4.9 |
| | $1.0 \cdot 10^{-6}$ | 1.9 |
| | $1.0 \cdot 10^{-8}$ | 3.0 |
| Ala—Lys—Asp—Val | $1.0 \cdot 10^{-4}$ | 0.04 |
| | $1.0 \cdot 10^{-6}$ | 0.01 |

The data of Table 1 show that the E-rosette forming activity of the lymphocytes of patients suffering from rheumatoid arthritis is significantly stimulated by the tetrapeptide Arg-Lys-Asp-Val (compound No. 2), its amide (compound No. 4), the tripeptide Arg-Lys-Asp (compound No. 3), the tetrapeptide Lys-Arg-Asp-Val (compound No. 5), the tetrapeptide Arg-Lys-Asu-Val (compound No. 10) in a concentration of $10^{-9}$ moles/lit., and a $10^{-11}$ moles/lit. dose of the compound of No. 5 and a $10^{-7}$ moles/lit. dose of the tetrapeptide ester Arg-Lys-Asp-Val-OMe also has a stimulating effect. The penta- and tetrapeptides starting with pyroglutamic acid (compounds Nos. 7 and 8) in a concentration of $10^{-9}$ and $10^{-5}$ moles/lit., respectively, as well as the tetrapeptide containing asparagine (compound No. 9) in a concentration of $10^{-5}$ moles/lit. show a significant inhibiting activity.

According to the data of Table 2 on the E-rosette forming activity of the lymphocites of healthy persons the tetrapeptide Arg-Lys-Asp-Val (compound No. 2) in a concentration of $10^{-9}$ moles/lit., the tripeptide Arg-Lys-Asp (compound No. 3) in a concentration of $10^{-7}$ moles/lit., the tetrapeptide Ala-Lys-Asp-Val (compound No. 6) in a concentration of $10^{-7}$ moles/lit. and the tetrapeptide Arg-Asp-Lys-Val (compound No. 8) in a concentration of $10^{-9}$ moles/lit. have a significant stimulating effect. The amide of the compound No. 2 (compound No. 4) in a concentration of $10^{-11}$ moles/lit., the tetrapeptide Arg-Lys-Asp-Ala (compound No. 5) and the tetrapeptide Glp-Arg-Lys-Asp (compound No. 9), both in a concentration of $10^{-11}$ moles/lit. have a stimulating effect as well. In this test the methyl ester of the compound No. 2 (compound No. 7) when employed in a concentration of $10^{-11}$ moles/lit. shows an inhibiting effect.

The in vivo effect on the antibody production, expressed in agglutination titers is illustrated in Table 3. It can be seen that the tripeptide Arg-Lys-Asp in a concentration of $4.10^{-6}$ moles/lit., the tetrapeptide Arg-Lys-Asp-Ala in a concentration of $4.10^{-7}$ moles/lit. as well as Arg-Lys-Asp-Val-NH$_2$ in a concentration of $4.10^{-8}$ moles/lit. have a significant stimulating activity. The two peptides in which the sequence is started with pyroglutamic acid, i.e. Glp-Arg-Lys-Asp-Val (in a concentration of $4.10^{-7}$ moles/lit.) and Glp-Arg-Lys-Asp-Val-Tyr (in a concentration of $2.10^{-3}$ moles/lit.) showed an inhibiting activity also in this test.

The results of the in vivo effect on plaque forming spleen cells are set forth in Table 4. According to these data the tripeptide Arg-Lys-Asp and the tetrapeptide amide Arg-Lys-Asp-Val-NH$_2$ in lower doses resulted in an about two-times increase while the tetrapeptide Arg-Lys-Asp-Ala induced a substantial increase in all tested dose. In the doses tested the tetrapeptide Ala-Lys-Asp-Val had a significant inhibiting activity.

The peptides according to the invention as well as their salts and complexes can be employed in the therapy in the form of conventional pharmaceutical preparations. The pharmaceutical compositions contain the active compounds according to the invention in admixture with inorganic or organic carriers suitable for enteral or parenteral administration. Typical pharmaceutical formulations include solid lyophilizates containing carriers not reacting with peptides, e.g. hydrocarbons, dilute or concentrated suspensions or emulsions, tablets or injection preparates, etc.

Our invention will further be illustrated by the following Examples which are for illustration and not for limitation of the invention.

The abbreviations and symbols used in the Examples are widely used in the chemical literature [J. Biol. Chem. 247,977 (1972)]. Further symbols:
Z=benzyloxycarbonyl,
Boc=tert.-butyloxycarbonyl,
O$^t$Bu=tert.-butyloxy,
OPfp=pentafluorophenoxy,
Asu=L-amino-succinyl,
OMe=methoxy,
OBzl=benzyloxy,
ONB=4-nitrobenzyloxy.

The melting points were determined in a Tottoli apparatus (Büchi, Switzerland). The t.l.c. measurements were performed on a silica gel absorbent (DC Fertigplatten, Merck), using the following solvent mixtures:
1. ethyl acetate:(pyridine:acetic acid:water=20:6:11)=95:5
2. ethyl acetate:(pyridine:acetic acid:water=20:6:11)=9:1
3. ethyl acetate:(pyridine:acetic acid:water=20:6:11)=4:1
4. ethyl acetate:(pyridine:acetic acid:water=20:6:11)=3:2
5. n-butanol:(pyridine:acetic acid:water=20:6:11)=3:7
6. chloroform:methanol=9:1
7. n-butanol:acetic acid:water=1:1:1
8. n-butanol:acetic acid:water=4:1:5, upper phase.

The chromatograms were developed by ninhydrine or after chlorination with KJ-tolydine. The specific optical rotatory power was determined by a Perkin-Elmer 141 photoelectric polarimeter. The solvents have been eliminated (evaporated) on a Büchi Rotavapor evaporator, on water bath the temperature of which did not exceed 40° C.

EXAMPLE 1 (METHOD A)

Z-Arg(NO$_2$)-Lys(Z)-Asp(OBzl)-Val-ONB

To a solution of 1.73 g. (6 mmoles) of Val-ONB.HCl in 15 ml. of dimethyl formamide 0.84 ml. (6 mmoles) of triethyl amine and 2.45 g. (5 mmoles) of Boc-Asp(OBzl)-OPfp are added. The reaction mixture is stirred at room temperature for 30 minutes, the solution is evaporated and the residue is dissolved in 30 ml. of ethyl acetate. The solution is subsequently shaken with 15-ml. portions of a 1 N aqueous hydrochloric acid solution, 5% aqueous sodium hydrocarbonate solution and water, dried over anhydrous sodium sulfate and evaporated in vacuo. The protected dipeptide obtained as a residue (R$_f^6$=0.9) is allowed to stand in 10 ml. of a 8 N solution of hydrochloric acid in dioxane and after 15 minutes is diluted with 40 ml. of anhydrous ether and evaporated to dryness. The residual free dipeptide (R$_f^2$=0.5) is dissolved in 10 ml. of dimethyl formamide, the pH is adjusted to 8 with triethyl amine and 3.1 g. (5.5 mmoles) of Boc-Lys(Z)-OPfp are added. The reaction mixture is stirred at room temperature for 30 minutes keeping the pH of the solution at 8 by adding triethyl amine. The solution is then diluted with 60 ml. of chloroform and is subsequently shaken with 15-ml. portions of a 1 N aqueous hydrochloric acid solution and water, respectively. The organic phase is dried and evaporated to dryness and the residue is solidified by adding dry ether. The protected tripeptide obtained (R$_f^1$=0.4) is precipitated by 100 ml. of dry ether, filtered and washed twice with ether. The product obtained is dissolved in 20 ml. of dimethyl formamide, the pH of the solution is adjusted to 8 with triethyl amine and 3.3 g. (7 mmoles) of Z-Arg(NO$_2$)-OPfp are added. The reaction mixture is stirred at room temperature for 30 minutes, keeping the pH at 8 with triethyl amine. The solvent is then evaporated, the residue is triturated with 50 ml. of ethanol, filtered and washed with two 10-ml. portions of ethanol. 3.05 g. of the corresponding protected tetrapeptide are obtained [yield: 73% related to the starting Boc-Aso(OBzl)-OPfp]. Melting point: R$_f^2$=0.80.

EXAMPLE 2 (METHOD B)

Z-Arg(NO$_2$)-Lys(Z)-Asp(PBzl)-OBzl

A mixture of 1.62 g. (3.3 mmoles) of Boc-Lys(Z)-OPfp, 1.40 g. (4.0 mmoles) of Asp(OBzl)-OBzl.HCl and 0.98 ml. (7.0 mmoles) of triethyl amine in 10 ml. of ethyl acetate is allowed to stand at room temperature for one hour. The reaction mixture is diluted with 20 ml. of ethyl acetate, shaken with 10 ml. of a 1 N aqueous acid solution and 10 ml. of an 5% aqueous sodium hydrocarbonate solution, dried over anhydrous sodium sulfate, the solvent is evaporated in vacuo and the residue is solidified with n-hexane, filtered and washed with n-hexane. The protected dipeptide obtained (yield: 81.2%; melting point: 92°-95° C., R$_f^2$=0.75) is treated with 30 ml. of a 4 N solution of hydrochloric acid in dioxane and after 30 minutes the solution is evaporated to dryness. The free dipeptide (R$_f^2$=0.10) is dissolved in 10 ml. of dimethyl formamide, the solution is neutralized with 0.35 ml. of triethyl amine whereupon the suspension obtained is added to a mixed anhydride prepared as follows: A solution of 10.6 g. (3.0 mmoles) of Z-Arg(NO$_2$)-OH and 0.42 ml. (3.0 mmoles) of triethyl amine in 5 ml. of dimethyl formamide is cooled to −10° C. To the solution 0.36 ml. (3.0 mmoles) of pivaloyl chloride are added dropwise at this temperature. To the mixed anhydride solution obtained the addition of the solution of free dipeptide is started after 5 minutes, at −10° C. The reaction mixture is stirred at 0° C. for further 30 minutes, allowed to stand at room temperature overnight and evaporated to dryness. The residue is dissolved in 50 ml. of chloroform and is subsequently shaken with 10-ml. portions of a 1 N hydrochloric acid solution, 5% aqueous sodium hydrocarbonate solution and water. The organic phase is dried and evaporated to dryness, and the residue is solidified with a 1:1 mixture of ether and n-hexane. 1.82 g. (84%) of the protected tripeptide given in the title are obtained R$_f^2$=0.70.

EXAMPLE 3 (METHOD C)

Z-Arg(NO$_2$)-Lys(Z)-Asu-Val-OH 2.51 g. (12 mmoles) of Val-O$^t$Bu.HCl are dissolved in 50 ml. of chloroform and 3.86 g. (10 mmoles) of Boc-Asp(O$^t$Bu)-OSu are added, followed by the addition of 1.68 ml. (12 mmoles) of triethyl amine. On the following day the solution is shaken with three 10-ml. portions of a 1 N aqueous hydrochloric acid solution and a 5% aqueous sodium hydrocarbonate solution, respectively. After drying the solvent is evaporated and the residual protected dipeptide ($R_f^2=0.80$) is allowed to stand in 30 ml. of a 5 n solution of hydrogen bromide in acetic acid for a week. The reaction mixture is then evaporated to dryness and the residue is solidified with dry ether. 2.65 g. (98.2%) of Asu-Val-OH.HBr($R_f^4=0.15$) are obtained which are acylated as described in Example 1. The characteristics of the protected tetrapeptide obtained are to be found in Table 5.

EXAMPLE 4

Arg-Lys-Asp-Val 2.25 g. (2.22 mmoles) of Z-Arg($NO_2$)-Lys(Z)-Asp(OBzl)-Val-ONB (Example 1) are suspended in 50 ml. of a 90% acetic acid solution, whereupon 1 g. of a 5% palladium-on-activated carbon catalyst are added and hydrogen gas is bubbled through the mixture for 14 hours. The catalyst is filtered off, washed with two 10-ml. portions of a 90% acetic acid solution and the filtrate is evaporated to dryness. The residue is evaporated again with water and ethanol, whereupon it is dissolved in 2 ml. of water and 30 ml. of ethanol are subsequently added. The suspension obtained is filtered and the precipitate is washed with ethanol. 0.92 g. (80%) of free tetrapeptide monoacetate are obtained.

Amino acid analysis: Lys 1.05 (1.00); Arg 0.95 (1.00); Asp 1.04 (1.00); Val 0.95 (1.00).

$(\alpha)_D^{22} = -24.8°$ (c=1.0, 10% acetic acid); $R_f^8=0.10$.

Following the methods A, B and C, respectively, as illustrated above but starting from equimolar amounts of the corresponding other starting materials the compounds of analogous structure shown in Tables 5 and 6 are obtained.

TABLE 5

The preparation and properties of protected peptides

| | Yield (%) total | Yield (%) stepwise | Method | Melting point (°C.) | $R_f$ | Purification |
|---|---|---|---|---|---|---|
| 1. Z—Arg($NO_2$)—Lys(Z)—Asp(OBzl)—Val—ONB | 73 | 90 | A | 135–148 | 0.80 (2) | 80% acetic acid |
| 2. Z—Arg($NO_2$)—Lys(Z)—Asp(OBzl)—OBzl | 68 | 82 | B | amorph | 0.70 (2) | ether/n-hexane (washing) (1:2) |
| 3. Z—Arg($Z_2$)—Lys(Z)—Asp(OBzl)—Val—$NH_2$ | 52 | 81 | A | 214–216 | 0.70 (2) | ethanol (boiling) |
| 4. Z—Lys(Z)—Arg($NO_2$)—Asp(OBzl)—Val—ONB | 78 | 92 | A | 117–120 | 0.60 (2) | ethanol/ether (1:2) |
| 5. Z—Arg($NO_2$)—Lys(Z)—Asp(OBzl)—Val—OMe | 52 | 80 | B | 125–135 | 0.60 (2) | ethanol |
| 6. Z—Glp—Arg($NO_2$)—Lys(Z)—Asp(OBzl)—Val—ONB | 59 | 84 | A | 166–172 | 0.80 (3) | ethanol |
| 7. Z—Glp—Arg($NO_2$)—Lys(Z)—Asp(OBzl)—OBzl | 60 | 85 | A | 100–104 | 0.60 (2) | ethanol/ether (1:2) |
| 8. Z—Arg($Z_2$)—Lys(Z)—Asn—Val—OBzl | 41 | 74 | A | 193–195 | 0.70 (3) | ethanol (boiling) |
| 9. Z—Ala—Lys(Z)—Asp(OBzl)—Val—ONB | 80 | 93 | A | 174–176 | 0.80 (1) | ethanol |
| 10. Z—Arg($NO_2$)—Ala—Asp(OBzl)—Val—ONB | 60 | 95 | A | 184–186 | 0.30 (1) | 90% ethanol |
| 11. Z—Arg($NO_2$)—Lys(Z)—Ala—Val—ONB | 68 | 87 | A | 157–159 | 0.45 (1) | 60% acetic acid |
| 12. Z—Arg($NO_2$)—Lys(Z)—Asu—Val—OH | 62 | 85 | C, A | 94 (b) | 0.30 (3) | ethanol/ether (1:4) |
| 13. Z—Arg($NO_2$)—Lys(Z)—Asp(OBzl)—Ala—ONB | 50 | 80 | A | 124–126 | 0.45 (1) | 60% acetic acid |
| 14. Z—Arg($NO_2$)—Lys(Z)—Asp(OBzl)—Ile—OBzl | 64 | 86 | B | 136–138 | 0.70 (2) | ethanol |
| 15. Z—Arg($NO_2$)—Asp(OBzl)—Lys(Z)—Val—OBzl | 42 | 75 | B | 136–141 | 0.65 (2) | ethyl-acetate |
| 16. Z—Glp—Arg($NO_2$)—Lys(Z)—Asp(OBzl)—Val—Tyr Bzl—ONB | 68 | 87 | A | 199–205 | 0.80 (3) | 60% acetic acid |
| 17. Z—Arg($NO_2$)—Lys(Z)—Glu(OBzl)—4-(Cl)—Val—OBzl | 39 | 73 | B | 124–127 | 0.65 (2) | ethyl-acetate |

TABLE 6

Properties of the free peptides

| | Yield (%) | $R_f$ | $(\alpha)_D^{22a}$ |
|---|---|---|---|
| 1. Arg—Lys—Asp—Val.AcOH[b] | 80 | 0.10 (8) | −24.8 |
| 2. Arg—Lys—Asp.AcOH | 83 | 0.20 (7) | 0 |
| 3. Arg—Lys—Asp—Val—$NH_2$.2AcOH | 84.3 | 0.20 (7) | −26.5 |
| 4. Lys—Arg—Asp—Val.AcOH | 77 | 0.30 (5) | −39.5 |
| 5. Arg—Lys—Asp—Val—OMe.2AcOH | 84.6 | 0.35 (5) | −28.3 |
| 6. Glp—Arg—Lys—Asp—Val[b] | 93 | 0.40 (5) | −51.3 |
| 7. Glp—Arg—Lys.AcOH[b] | 70 | 0.35 (5) | −31.4 |
| 8. Arg—Lys—Asn—Val.2AcOH | 79.5 | 0.10 (5) | −23.0 |
| 9. Ala—Lys—Asp—Val.AcOH.$H_2O$ | 90 | 0.35 (5) | −38.6 |
| 10. Arg—Ala—Asp—Val | 87 | 0.45 (5) | −37.9 |
| 11. Arg—Lys—Ala—Val.3AcOH | 88.5 | 0.45 (5) | −34.6 |
| 12. Arg—Lys—Asu—Val.2AcOH | 68 | 0.15 (5) | −31.0 |
| 13. Arg—Lys—Asp—Ala.AcOH | 88 | 0.25 (5) | −19.9 |
| 14. Arg—Lys—Asp—Ile.AcOH | 48.6 | 0.15 (5) | −19.5 |
| 15. Arg—Asp—Lys—Val.AcOH | 89.2 | 0.25 (7) | −19.4 |
| 16. Glp—Arg—Lys—Asp—Val—Tyr[b] | 80.0 | 0.20 (8) | −51.5 |

TABLE 6-continued

| | Properties of the free peptides | | |
|---|---|---|---|
| | Yield (%) | $R_f$ | $(\alpha)_D^{22a}$ |
| 17. Arg—Lys—Glu—Val.AcOH | 97 | 0.30 (7) | −21.4 |

$^a$c = 1, in 10% acetic acid
$^b$Chromatography on Kieselgel SI-100 column with a 1:1 mixture of methanol and water
AcOH = acetic acid

We claim:

1. Peptides affecting the immune regulation selected from the following group:
Arg-Lys-Asp
Arg-Lys-Asp-Val
Arg-Lys-Asn-Val
Arg-Lys-Asu-Val
Arg-Lys-Ala-Val
Arg-Lys-Asp-Ala
Arg-Lys-Asp-Ile
Arg-Lys-Glu-Val
Arg-Ala-Asp-Val
Arg-Asp-Lys-Val
Ala-Lys-Asp-Val
Lys-Arg-Asp-Val
Glp-Arg-Lys-Asp
Glp-Arg-Lys-Asp-Val
Glp-Arg-Lys-Asp-Val-Tyr
and salts, amides, lower alkyl esters and protected derivatives thereof.

2. A method of treating an immunological disorder due to a deficiency in the thymus which comprises the step of administering to a subject in need of said treatment, a pharmaceutically effective amount of the compound defined in claim 1.

3. A method of regulating thymus hormonal levels, which comprises the step of administering to a subject in need of said regulation, a pharmaceutically effective amount of the compound defined in claim 1.

* * * * *